(12) United States Patent
Bobrow et al.

(10) Patent No.: US 11,767,498 B2
(45) Date of Patent: Sep. 26, 2023

(54) IN VITRO TISSUE PLATE

(71) Applicants: Massachusetts Institute of Technology, Cambridge, MA (US); The United States of America, as represented by the Secretary, Department of Health and Human Services, Bethesda, MD (US)

(72) Inventors: Johanna Bobrow, Somerville, MA (US); Todd Thorsen, Carlisle, MA (US); David Walsh, Boston, MA (US); Christina Zook, Tewksbury, MA (US); Min Jae Song, Laytonsville, MD (US); Marc Ferrer-Alegre, Potomac, MD (US); Sam Michael, Germantown, MD (US); Yen-Ting Tung, Derwood, MD (US); Molly Elizabeth Boutin, Troy, NY (US)

(73) Assignees: Massachusetts Institute of Technology, Cambridge, MA (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 438 days.

(21) Appl. No.: 16/912,941

(22) Filed: Jun. 26, 2020

(65) Prior Publication Data
US 2021/0062128 A1    Mar. 4, 2021

Related U.S. Application Data

(60) Provisional application No. 62/893,067, filed on Aug. 28, 2019.

(51) Int. Cl.
   *C12M 1/32* (2006.01)
   *B01L 3/00* (2006.01)
   (Continued)

(52) U.S. Cl.
   CPC ....... *C12M 23/12* (2013.01); *B01L 3/502715* (2013.01); *B01L 3/502738* (2013.01);
   (Continued)

(58) Field of Classification Search
   CPC ...... C12M 23/12; C12M 23/40; C12M 25/14; C12M 29/10; C12M 29/04; C12M 21/08;
   (Continued)

(56) References Cited

U.S. PATENT DOCUMENTS

2014/0271778 A1* 9/2014 Buensucceso .......... A61L 27/34
                                                          424/558
2020/0354668 A1* 11/2020 Sawyer .................. C12M 23/44

FOREIGN PATENT DOCUMENTS

WO    WO-2017216113 A2 * 12/2017  ........ B01L 3/502715

OTHER PUBLICATIONS

Goral et al. "A continuous perfusion microplate for cell culture". Lab on a Chip. vol. 13, pp. 1039-1043. 2013 (Year: 2013).*

(Continued)

*Primary Examiner* — Michael L Hobbs
(74) *Attorney, Agent, or Firm* — Wolf, Greenfield & Sacks, P.C.

(57) ABSTRACT

An in vitro tissue plate may include a well plate, a fluidic plate disposed on a bottom surface of the well plate, and a media manifold disposed on a bottom surface of the fluidic plate. The well plate may have at least two wells, including a tissue well and a waste well. The fluid plate may include a fluid channel extending between and fluidly connecting the tissue well to the waste well. The media manifold may include a one or more media outlets fluidly connected to the fluid channel. A tissue layer may be deposited in the tissue well. The tissue layer may include human cells such as neurovascular cells.

13 Claims, 10 Drawing Sheets

(51) Int. Cl.
*C12M 1/12* (2006.01)
*C12M 1/00* (2006.01)

(52) U.S. Cl.
CPC ............ *C12M 23/40* (2013.01); *C12M 25/14* (2013.01); *C12M 29/10* (2013.01); *B01L 2300/0829* (2013.01); *B01L 2300/0861* (2013.01)

(58) Field of Classification Search
CPC ......... B01L 3/502715; B01L 3/502738; B01L 3/5085; B01L 2300/0829; B01L 2300/0861; B01L 2300/0645; B01L 2300/0851
See application file for complete search history.

(56) References Cited

OTHER PUBLICATIONS

Oddo et al. Advances in Microfluidic Blood-Brain Barrier (BBB) Models. Trends Biotechnol. 2019;37(12):1295-1314. doi:10.1016/j.tibtech.2019.04.006.

* cited by examiner

IN VITRO TISSUE PLATE

RELATED APPLICATIONS

This application claims the benefit of 35 U.S.C. § 119(e) to U.S. Provisional Application Ser. No. 62/893,067, filed Aug. 28, 2019, which is herein incorporated by reference in its entirety.

GOVERNMENT LICENSE RIGHTS

This invention was made with Government support under FA8702-15-D-0001 awarded by the U.S. Air Force. The Government has certain rights in the invention.

FIELD

Disclosed embodiments are related to an in vitro tissue plate and related methods of use.

BACKGROUND

Conventionally, therapeutic studies of neurological and other disorders are performed on animals. These studies oftentimes have long development cycles, and inhibit rapid iteration. Additionally, animal studies sometimes have limited applicability to human use, resulting in failed trials at a late stage in therapy development. To address this, organ-on-chip systems have been developed to model different body structures for the study of therapeutic disorders for a variety of human organs.

SUMMARY

In some embodiments, an in vitro tissue plate includes a well plate including at least two wells, where the at least two wells include a tissue well and a waste well. The in vitro tissue plate also includes a fluidic plate disposed on a bottom surface of the well plate, where the fluidic plate includes a fluid channel extending between and fluidly connected to the tissue well and the waste well.

In some embodiments, an in vitro tissue plate includes a well plate having an array of wells, where the array of wells includes a plurality of tissue wells and one or more waste wells associated with the plurality of tissue wells, and a fluidic plate disposed on a bottom surface of the well plate. The fluidic plate includes a plurality of fluid channels, where each tissue well is fluidly connected to an adjacent waste well by one of the plurality of fluid channels.

In some embodiments, a method of using an in vitro tissue plate includes depositing a tissue layer in a first tissue well formed in a well plate, and supplying feed media into a first fluid channel positioned below the first tissue well. The method also includes allowing the tissue layer to vascularize in a flow of the feed media, and collecting waste media from the first fluid channel into a first waste well.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
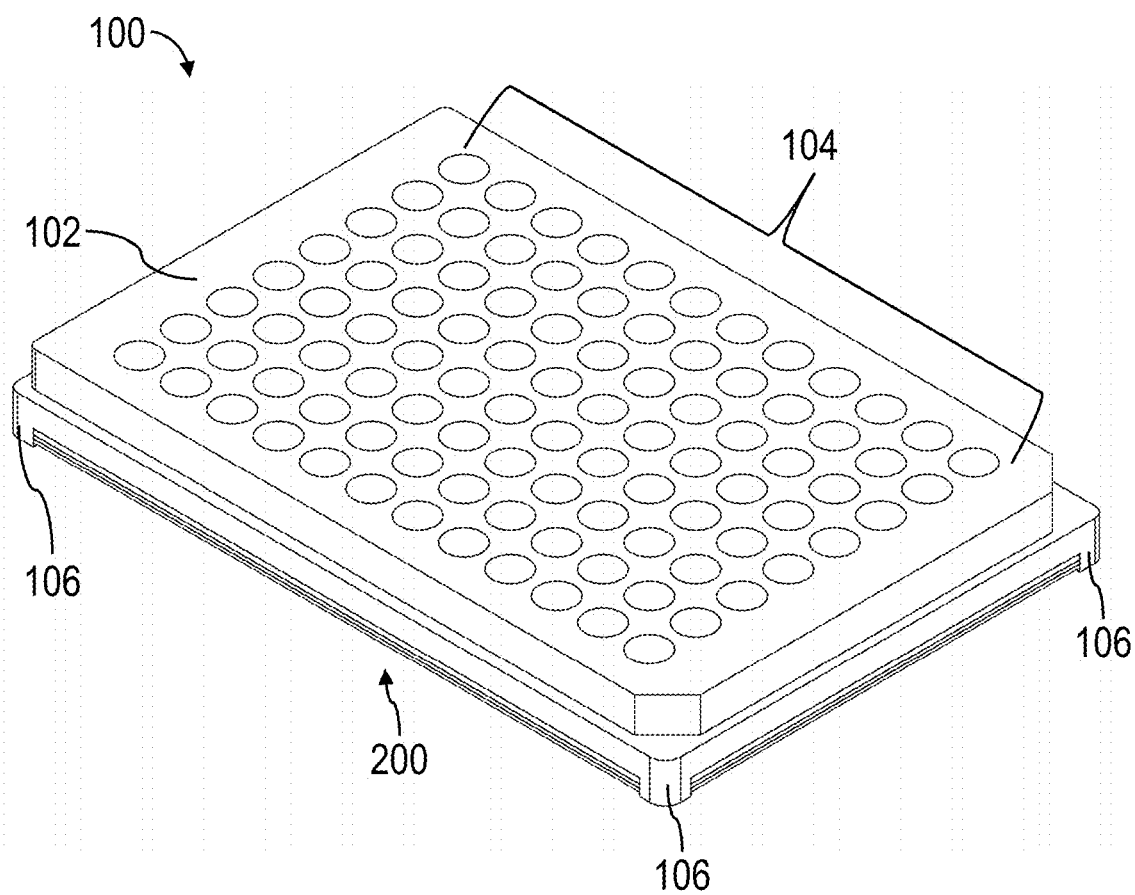
FIG. 1 is a perspective view of one embodiment of an in vitro tissue plate.

Therapeutic options for neurological disorders currently remain limited. Specifically, the complexity of the brain architecture, and the blood-brain barrier in particular, limits the efficacy of potential therapeutics. Most commonly, costly time consuming animal tests are performed for evaluating potential therapeutics, which can inhibit rapid iteration and development of these potential therapeutics. Moreover, animals are sometimes poor or unreliable predictors for human use, and many potential therapeutics which show success in animal trials fail in human trials. To address this, some organ-on-chip or system-on-chip (SOC) devices have been developed to address some of the concerns with animal testing. However, many of these conventional SOC devices operate on a miniaturized scale that may be unrepresentative of the scale at which structures in the human body operate, and accordingly may also yield unreliable results. Additionally, these SOC devices may be incompatible with existing laboratory analysis and automation equipment, making their deployment cost prohibitive.

In view of the above, the inventors have recognized the benefits of an in vitro tissue plate which allows for rapid testing of therapeutic compounds at scales representative of structures in the human body. Such an in vitro tissue plate may be more reliable than existing SOC devices and animal tests, and may allow a greater scope of tests to be conducted rapidly. The inventors have also recognized the benefits of an in vitro tissue plate which may be used with current laboratory analysis equipment. Such an arrangement may allow the tissue plate to be easily deployed at scale in existing labs. The inventors have also recognized the benefits of an in vitro tissue plate that is simple to manufacture, assemble, and use. Though instances in which the disclosed methods and systems exhibit only some and/or different benefits than those noted above are also contemplated, as the disclosure is not limited in this fashion.

In some embodiments, an in vitro tissue plate includes a well plate, a fluidic plate, and a media manifold that cooperate to model a neurological or other appropriate body tissue or structure. The in vitro tissue plate may allow for nutrient delivery and waste removal while permitting vascularization to occur to form a model natural environment for the tissue. The well plate may include at least two wells, where the at least two wells have a tissue well and a waste well. The fluidic plate may be positioned on a bottom surface of the well plate opposite a top surface of the well plate which may include corresponding openings for the at least two wells. The fluidic plate may include a fluid channel which extends between and fluidly connects the tissue well to the waste well. The media manifold may be positioned on a bottom surface of the fluidic plate opposite the top surface of the fluidic plate located adjacent to the well plate. The media manifold may include a media supply channel fluidly connected to the fluid channel. The media manifold may be coupled to a supply of media (e.g., a pump), creating a flow path from the supply of media through the tissue well and to the waste well. The fluid channel in the fluidic plate may be fluidly connected to the tissue well via a plurality of tissue well pores, while the fluid channel may be fluidly connected to the waste well via one or more waste well pores. In some embodiments, the fluid channel may be continuous between the media supply channel and the waste well, such that the media flow through the fluid channel may bifurcate through a subset of the tissue well pores into the tissue well, and flow from the tissue well though a separate subset of the tissue well pores to rejoin the fluid channel. Such an arrangement may promote vascularization of living cells disposed in the tissue well.

As noted above, in some embodiments, a plurality of tissue well pores and one or more waste well pores may be formed in a separate pore plate. The separate pore plate may be disposed between a well plate (e.g., on a bottom surface of the well plate) and a fluid plate (e.g., on a top surface of the fluidic plate). Such an arrangement may simplify the manufacturing of the in vitro tissue plate, as each of the pores may be formed as a through-hole through the pore plate. In some cases, such an arrangement may be easily manufactured by 3D printing (e.g., SLA), laser cutting, injection molding, or any other appropriate manufacturing process. In some embodiments, a pore plate may be formed of polymethyl methacrylate (PMMA). Of course, the pore plate may be formed of any suitable biocompatible material, as the present disclosure is not so limited. In other embodiments, the pores may be formed in the well plate, the fluidic plate, or a combination thereof, and the pore plate may be omitted from the in vitro tissue well plate, as the present disclosure is not so limited.

In some embodiments, multiple plates of an in vitro tissue plate may stack to form one or more media flow paths through tissue wells and waste wells. In one embodiment, a well plate may be constructed such that it engages with, positions, and/or orients a pore plate, fluidic plate, and/or media manifold relative to the well plate such that the in vitro tissue plate is maintained in a desired configuration. For example, a plurality of supports, such as projections, recesses, or other appropriate structures, may be formed in the well plate, or other appropriate portion of the tissue barrier plate, to selectively engage, position, and/or orient the pore plate, fluidic plate, and/or media manifold relative to the well plate. When the supports receive one or more plates, the plates may be allowed to move along a single axis corresponding to a direction of extension of the supports. In some embodiments, the supports may project perpendicularly from a bottom surface of the well plate, thereby allowing the one or more plates, which may have corresponding structures that engage with the supports, to move toward or away from the bottom surface of the well plate while preventing rotation and/or translation of the plates in a different direction. Thus, the supports may maintain the orientation of the one or more received plates, and in some embodiments may maintain the one or more plates in an orientation where the one or more plates are parallel to the bottom surface of the well plate. In some embodiments, the supports may include tabs (e.g., latches, detents, compressive features, etc.) which engage a corresponding portion of an outer perimeter of the one or more received plates to releasably retain the one or more plates against the well plate. The retaining force applied by the tabs may be sufficient to compress the plates against one another to facilitate forming a fluidic seal between each layer and the well plate. Such an arrangement may allow an in vitro tissue plate to be easily assembled, used, and disassembled. In some embodiments, one or more of the plates may include a gasket (e.g., a rubber gasket), and/or a gasket may be positioned between adjacent plates, to further improve fluid sealing.

In some embodiments, one or more plates of an in vitro tissue barrier plate may include an imaging window to allow a tissue well and its contents to be monitored. For example, in one embodiment, a fluidic plate may include an imaging window formed as a hole for each corresponding tissue well in the well plate. The imaging window may be partially surrounded by the fluid channel, such that a flow path from the fluidic plate to the well plate is not interrupted or in communication with the imaging window. In some embodiments, a pore plate disposed between the fluidic plate and the well plate may be formed of a transparent material, such that an imaging device and/or optical sensor may monitor and/or image a tissue well through the pore plate. In some embodiments, a microscope may be used to monitor the tissue well. Of course, it should be understood that one or more imaging windows may be formed in any suitable portion of an in vitro tissue barrier plate to allow a tissue well to be viewed, sensed, and/or monitored, as the present disclosure is not so limited. In some embodiments, an imaging window may be employed to allow for high-resolution fluorescent assays of cells disposed in a tissue well and/or fluid channel below the tissue well.

In some embodiments, one or more sensors configured to sense one or more desired parameters may be integrated into or employed with the various exemplary embodiments of an in vitro tissue plate described herein. For example, in one embodiment, flexible polyimide electrodes may be integrated into a tissue plate to enable sensing of transendothelial electrical resistance and neuronal activity of cells disposed in a tissue well. Such an arrangement may allow the tightness of a tissue layer to be determined. Other sensors that may be employed include, but are not limited to, flow rate sensors, oxygen sensors, and/or any other appropriate sensor. In some embodiments, one or more plates of an in vitro tissue plate may include a hole or recess to accommodate one or more integrated sensors for sensing a desired parameter associated with the wells (or tissue well and waste well combination).

In some embodiments, one or more non-optical based sensors may be employed concurrently with one or more optical sensors for sensing various parameters associated with cells within a tissue well. In one such embodiment, two or more electrodes, or other sensors, that are optically transparent may be integrated into a tissue well plate so that electrical resistance, neuronal activity, and/or any other appropriate parameter of cells disposed in a tissue well may be measured. Concurrently, in some embodiments, optical sensors for imaging (e.g., high-resolution confocal imaging) or sensing other parameters of the tissue in the well plate may be employed, where the electrodes, or other sensors, do not interfere with the optical sensors imaging the cells within an associated well. For example, the one or more optical sensors may image the cells through the one or more optically transparent sensors. In view of the above, optically transparent electrodes, optically transparent conducting films, and/or other appropriate optically transparent components associated with one or more sensors may be integrated into any suitable portion of an in vitro tissue plate, such as a bottom plate or film, as the present disclosure is not so limited. In some embodiments, opaque electrodes and traces may be disposed on an optically transparent substrate to form an optically transparent electrode array that is integrated into a tissue well plate. In this manner, an optically transparent electrode array may allow optical sensors to sense parameters of tissue in a tissue well while allowing opaque electrodes to measure electrical resistance, neuronal activity, and/or any other appropriate parameter.

In some embodiments, one or more pumps may be employed with an in vitro tissue plate. A media supply pump may be coupled to a media manifold including a plurality of media supply channels, each of which is fluidly connected to a tissue well in a well plate. The media supply pump may pump media through each media supply channel and into the tissue well. The media supply pump may be connected to a flow splitter with a separate, selectable fluid connection to each of the individual media supply channels. Accordingly, each tissue well may be supplied with media at an individual rate and volume. In some embodiments, the flow splitter may be controlled such that media is supplied to each of the tissue wells in sequence. That is, one tissue well may be supplied with media at a time so that the flow rate and pressure may be controlled for that tissue well without influence from other tissue wells. Without wishing to be bound by theory, supplying multiple wells in parallel with a single pump may cause a majority of the media to flow to a lower pressure tissue well such that the flow rate and volume of media supplied to the wells is uneven. Accordingly, the flow splitter may be controlled to allow ensure consistent, repeatable flow rates and volumes of media across multiple tissue wells in a well plate. In some embodiments, the media supply pump may be a peristaltic pump, which may allow the volume and flow rate of media to be consistently controlled. Of course, any suitable pump may be employed with an in vitro tissue well plate, as the present disclosure is not so limited. In some embodiments, multiple pumps may be employed and/or any other appropriate arrangement capable of providing a desired flow rate of media to the individual wells. For example, each well may be fluidly connected to an individual pump. Of course, any suitable number of pumps, splitters, and/or other appropriate components capable of providing a flow of media to the one or more wells may be used as the present disclosure is not so limited.

In some cases, the flow rate and pressure of media supplied through an in vitro tissue plate may affect the development and vascularization of cells disposed in a tissue well. For example, shear stress on a tissue layer may improve the mass transport and cell development (e.g., vascularization). Accordingly, the flow rate of media supplied to the tissue plate (e.g., through a fluid channel) may be carefully controlled for each tissue well. In some embodiments, media may be supplied from a media supply pump to an in vitro tissue plate at a rate greater than or equal to 0.25 µL/sec, 0.5 µL/sec, 1 µL/sec, 1.5 µL/sec, 2.5 µL/sec, 4 µL/sec, 5 µL/sec, and/or any other appropriate flow rate. Correspondingly, media may be supplied from a media supply pump to an in vitro tissue plate at a rate less than or equal to 5 µL/sec, 4 µL/sec, 3 µL/sec, 2.5 µL/sec, 2 µL/sec, 1 µL/sec, 0.75 µL/sec, and/or any other appropriate flow rate. Combinations of the above noted values are contemplated including, but not limited to, 0.5 and 5 µL/sec, 1 and 2.5 µL/sec, as well as 1 and 4 µL/sec.

In some embodiments, media may be supplied from a media supply pump through a fluid channel such that a shear stress applied to a tissue layer disposed in a tissue well during media flow is greater than or equal to 0.5 dynes/$cm^2$, 1 dyne/$cm^2$, 1.5 dynes/$cm^2$, 2 dynes/$cm^2$, 5 dyne/$cm^2$, 7.5 dynes/$cm^2$, and/or any other appropriate shear stress. Correspondingly, shear stress may be less than or equal to 10 dynes/$cm^2$, 7.5 dynes/$cm^2$, 5 dynes/$cm^2$, 2.5 dynes/$cm^2$, 2 dynes/$cm^2$, 1.5 dynes/$cm^2$, and/or any other appropriate shear stress. Combinations of the above noted shear stresses are contemplated, including, but not limited to, 1 and 2 dynes/$cm^2$, 1 and 5 dynes/$cm^2$, as well as 2 and 7.5 dynes/$cm^2$. In some cases, spacing between tissue well pores may affect the shear stress applied to a tissue layer. In some embodiments, the spacing between tissue well pores adjacent a single tissue well may be greater than or equal to 0.1 mm, 0.25 mm, 0.5 mm, 0.75 mm, and/or any other appropriate distance. Correspondingly, the spacing between tissue well pores adjacent a single tissue well may be less than or equal to 1.5 mm, 1 mm, 0.75 mm, 0.5 mm, 0.25 mm, and/or any other appropriate distance. It should be understood that the above noted ranges may be combined in any appropriate fashion, and that ranges both greater than and less than those noted above may be used with the currently disclosed embodiments, as the disclosure is not so limited.

As media flows through one or more tissue wells, a tissue layer disposed in the wells may excrete waste that may be collected in one or more corresponding waste wells. To ensure the development of a tissue layer and to avoid cytotoxic conditions, this waste may be removed from the waste well. In some embodiments, this waste may be removed via drain channels or pumping. In one such embodiment, a waste extraction pump may be employed with an in vitro tissue plate to remove waste from one or more waste wells of a well plate. The waste extraction pump may be fluidly connected to the waste wells via a top cap which is disposed on a top surface of a well plate (e.g., a side opposite a pore plate, fluidic plate, and/or media manifold). The waste extraction pump may remove waste from the waste well as media is supplied to the tissue well. Accordingly, the waste extraction pump may cooperate with the media supply pump so that a consistent flow rate from the media supply pump, through the tissue well and waste well, and to the waste extraction pump may be provided. Similarly to the media supply pump, the waste extraction pump may sequentially remove waste from each of the waste wells in a well plate, such that consistent and repeatable flow rates may be used for each tissue well and waste well pair.

According to exemplary embodiments described herein, an in vitro tissue plate may include human cells disposed in the one or more tissue wells. In some embodiments, a tissue layer (e.g., barrier tissue) may be deposited into a tissue well of a well plate. The tissue layer may include a mixture of a hydrogel, living cells, and/or any other appropriate mixture. In one embodiment, the living cells may include neurovascular cells (e.g., to simulate a blood-brain barrier). In some embodiments, a 6e6 cells/mL bioink may be mixed with the hydrogel and deposited in a tissue well. Such a mixture may be appropriate to allow the living neurovascular cells to vascularize in a flow of media. Of course, any suitable cell mixture may be employed, as the present disclosure is not so limited.

According to exemplary embodiments described herein, an in vitro tissue plate may include one or more plates formed of different materials. For example, in one embodiment, a well plate and fluidic plate may be formed of a three dimensional (3D) printed material including plastic or rubber. The 3D printed material may be coated with parylene-C wax, using vapor deposition for example, and/or the material may be exposed to ultraviolet ozone (UVO) and/or oxygen plasma treatment to inhibit cytotoxicity of the 3D printed material. In other embodiments, one or more plates (e.g., a pore plate) may be formed of PMMA or another optically transparent polymeric material. Of course, any appropriate non-cytotoxic material or cytotoxic material coated with a non-cytotoxic coating may be employed, which may be manufactured using any suitable method, including, but not limited to, 3D printing, injection molding, machining, and laser cutting, as the present disclosure is not so limited. Further, embodiments in which non-optically transparent materials are used for one or more components of the disclosed in vitro tissue plates are also contemplated as the disclosure is not limited in this fashion.

In some embodiments, a method of using an in vitro tissue plate includes depositing a tissue layer in a tissue well of a well plate. The tissue layer may be bioprinted, and may include both a hydrogel and a plurality of living cells. Though, it should be understood that the tissue layer deposited into a tissue well may include any appropriate mixture of materials and may be deposited in any appropriate fashion. In some embodiments, the living cells include neurovascular cells. Other appropriate types of tissues cells that may be included in a tissue well for modeling a desired type of tissue may include, but is not limited to, lung, skin, blood-brain-barrier, blood-retina-barrier, GI-tract, kidney, and any type of barrier tissue (e.g., epithelial tissue). The method may also include supplying feed media into a fluid channel positioned below the tissue well, where the fluid channel is fluidly connected to the tissue well by a plurality of pores. Supplying the feed media into the fluid channel may allow the living cells to vascularize, and the feed media may bifurcate into flows through the fluid channel and flows through the pores and tissue layer. The flows through the pores and vascularized tissue may flow through other pores to rejoin the fluid channel. The method also includes collecting waste media from the fluid channel into a waste well formed in the well plate. Finally, the method may include extracting the waste media from the waste well through a top opening of the waste well. For example, a top cap including one or more appropriate features such as pipettes, tubing, channels, and/or any other appropriate construction may be used to extract the waste media from the one or more waste wells with a waste extraction pump.

As described previously, in some cases it may be desirable to supply a plurality of tissue wells with feed media in sequence. Without wishing to be bound by theory, supplying a plurality of wells with feed media simultaneously may result in different flow rates to each well, which may result in inconsistent results of tests between wells. Accordingly, in some embodiments, a flow splitter may be employed to supply feed media to each of a plurality of wells individually in sequence. In one embodiment, flow may be supplied to a first tissue well for approximately 10 seconds, whereupon the flow may be switched to a second tissue well and supplied for approximately 10 seconds. This sequence may be repeated for an entire well plate, or a desired sub-portion of a well plate, until each tissue well associated with a particular pump and flow splitter has been supplied with feed media and the cycle begins again. In some embodiments, this overall cycle may be continuously repeated for the duration of a therapeutic test. In some embodiments, a tissue well may be supplied with a flow of media for a duration greater than or equal to 1 second, 2 seconds, 5 seconds, 10 seconds, 15 second, 25 seconds, and/or any other appropriate duration. Correspondingly, a tissue well may be supplied with a flow of media for a duration less than or equal to 30 seconds, 25 seconds, 20 seconds, 15 seconds, 10 seconds, 5 seconds, and/or any other appropriate duration. In addition to the durations of media flow provided to individual tissue wells, any appropriate duration may be selected for times between media being provided to the individual walls. For example, a duration between cycles of media being provided to individual tissue wells may be less than or equal to 10 minutes, 8 minutes, 6 minutes, 4 minutes, 1 minute, and/or any other appropriate duration. Correspondingly, a duration between cycles of media being provided to individual tissue wells may be greater than or equal to 30 seconds 1 minute, 2 minutes, 4 minutes, and/or any other appropriate duration. Combinations of the foregoing ranges for the cyclic sequential application of media flow to the individual tissue wells are contemplated. Further, it should be understood that embodiments in which media is continuously flowed to one or more tissue wells of an in vitro tissue plate rather than being applied in a sequential fashion are also contemplated as the disclosure is not limited in this fashion.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 is a perspective view of one embodiment of an in vitro tissue plate 100. As shown in FIG. 1, the tissue plate 100 includes a well plate 102 and a plurality of supporting plates 200, which cooperate to form fluid channels appropriate for forming vascularized neurological tissue. According to the embodiment shown in FIG. 1, the well plate 102 includes a plurality of wells 104 which are arranged in an array of rows and columns. In particular, in the embodiment of FIG. 1, the wells are arranged in 12 columns and 8 rows to form a 96-well microtiter plate. Each of the wells may have a working volume of approximately 75-200 μL. Each of the wells may have a diameter of 6.94 mm, and spacing between the centers of adjacent wells of 9 mm. Accordingly, in some embodiments, the well plate 102 of FIG. 1 may be compatible with the ANSI SLAS Standards 1-4 (2004), such that the well plate is compatible with existing laboratory measurement and automation According to the embodiment of FIG. 1, the well plate 102 includes a plurality of supports 106 that are disposed on each corner of the well plate. The supports extend downward from a bottom surface of the well plate. The supports are configured to engage corresponding portions of each of the supporting plates 200 to maintain an orientation and position of the supporting plates relative to the well plate 102. That is, the supports 106 may help maintain each of the supporting plates 200 disposed in planes parallel to the plane of the well plate 102. In some embodiments, the supports 106 may include one or more tabs to retain each of the plurality of supporting plates adjacent the well plate. That is, the supports may retain the supporting plates flush with a bottom surface of the well plate. In some embodiments, the supporting plates 200 may be bonded together. For example, the supporting plates may be bonded together using double-sided adhesive (e.g., laser cut double-sided adhesive), glue, or another suitable bonding agent.

Figure 2:
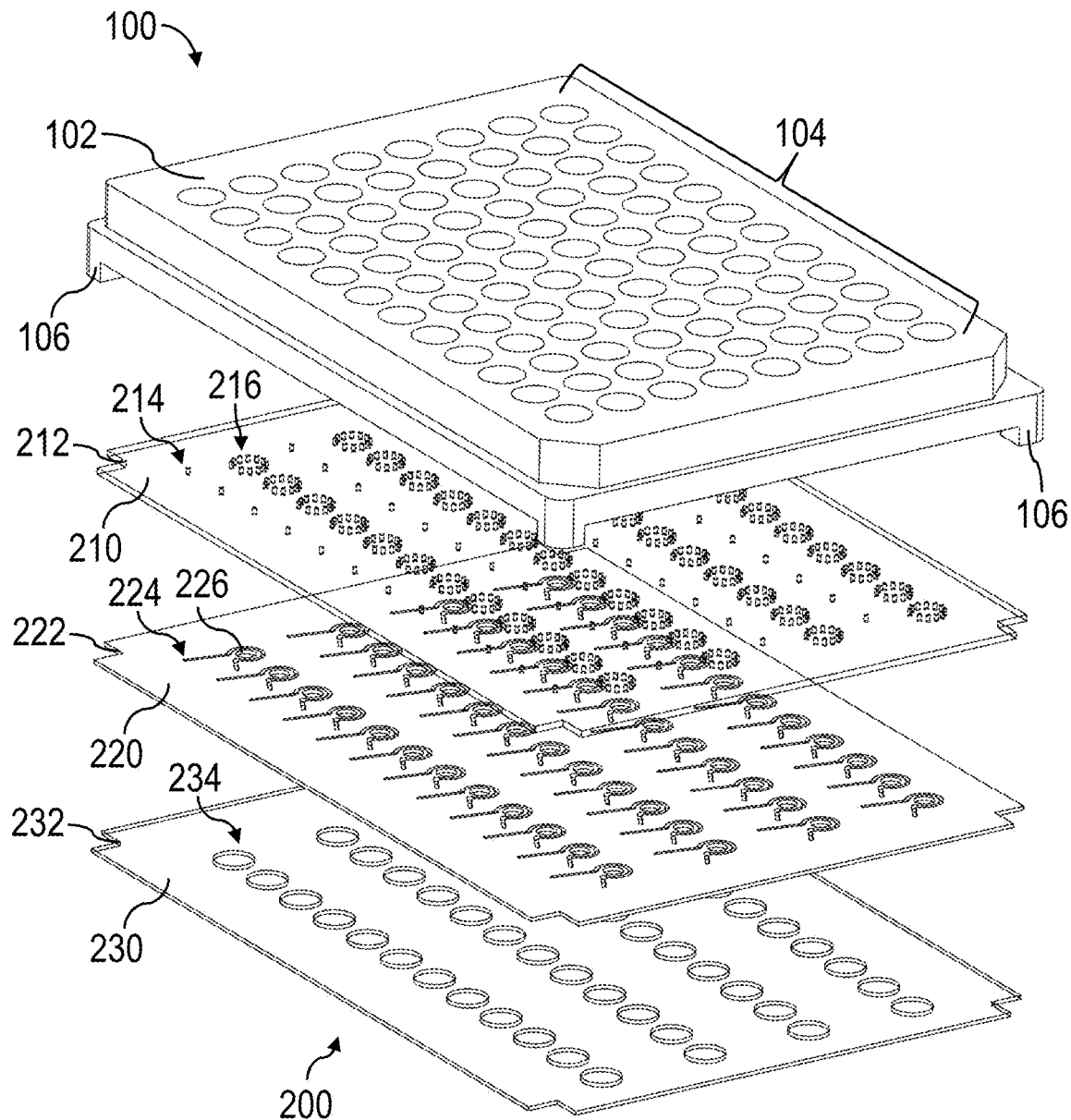
FIG. 2 is an exploded view of the tissue plate of FIG. 1.

FIG. 2 is an exploded view of the tissue plate 100 of FIG. 1, showing each of the supporting plates 200 that form the fluid channels which allow a tissue layer disposed in a portion of the wells 104 to vascularize under feed media flow. According to the embodiment shown in FIG. 2, the tissue plate includes a pore plate 210, a fluidic plate 220, and a bottom holding plate 230. Each of the supporting plates 200 includes cutouts 212, 222, 232 configured to receive supports 106 of the well plate 102. In the embodiment of FIG. 2, the supports 106 and cutouts 212, 222, 232 are rectangular in shape and complement a shape of one another, such that the orientation of each of the supporting plates 200 is maintained when the cutouts receive the supports. Of course, the cutouts and supports may have any appropriate shape to align and orient the supporting plates 200 relative to the well plate 102, as the present disclosure is not so limited.

As shown in FIG. 2, the pore plate 210 is configured to be positioned on a bottom surface of the well plate 102. The pore plate includes a plurality of waste well pores 214 and a plurality of tissue well pores 216. In the embodiment of FIG. 2, the pore plate includes at least one waste well 214 for each waste well of the well plate 102. For each tissue well of the well plate 102, the pore plate includes a plurality of tissue well pores 216, which improves vascularization of a tissue layer. The tissue well pores are positioned annularly adjacent to each tissue well. The pores of the pore plate are configured to fluidly connect each of the wells 104 to a fluid channel 224 of the fluidic plate 220. The pore plate may also function to fluidly seal a bottom of each well 104. That is, the well 104 may be open on both the top and bottom to simplify cleanout of the well, and the pore plate 210 may function as the well bottom. As shown in FIG. 2, the pore plate 210 may be composed of a transparent material (e.g., PMMA) which allows cells disposed in the wells 104 to be observed from below the pore plate 210. However, embodiments in which the pores are formed directly in a bottom surface of the well plate are also contemplated.

The fluidic plate 220 is configured to be positioned on a bottom surface of the pore plate 210, and/or, in some embodiments, a bottom surface of a well plate with pores formed therein. The fluidic plate includes a plurality of fluid channels 224. The fluid channels may be formed as through slots in the fluidic plate. That is, the fluid channel may extend from a top surface of the fluidic plate through to an opposing bottom surface of the fluidic plate. In some embodiments, the fluid channel has a width of approximately 0.5 mm and the fluidic plate has a depth of approximately 0.5 mm. As the fluid channel may be formed through fluidic plate 220, manufacture of the fluidic plate may be simplified through laser cutting, 3D printing, and/or molding as no covered internal channels are employed. In some embodiments, a fluid channel may have a cross-section with a width and/or thickness that is greater than or equal to 0.1 mm, 0.25 mm, 0.35 mm, 0.5 mm, 0.75 mm, 1 mm, and/or any other appropriate dimension. Correspondingly, a fluid channel may a cross-section with a width and/or thickness that is less than or equal to, 1.5 mm, 1 mm, 0.75 mm, 0.6 mm, 0.5 mm, 0.35 mm, and/or any other appropriate dimension.

Similarly to the pore plate 210, the fluid channels 224 may be sealed on either side (e.g., top and bottom surfaces) by adjacent plates. On the top surface the pore plate 210 may seal the fluid channels, while on the bottom surface the separate bottom holding plate 230 may seal the fluid channels. As shown in FIG. 2, the fluid channels 224 may have a semi-annular portion aligned with the plurality of tissue well pores 216 of the well plate 102, such that each fluid channel is brought into communication with a tissue well of the well plate through the plurality of pores. Likewise, an end of the fluid channel may be aligned with a waste well pore 214 such that each fluid channel is fluidly connected with a waste well of the well plate. In some embodiments, the fluidic plate 220 may be formed of an opaque or otherwise non-transparent material which inhibits observation of the wells from a bottom surface of the fluidic plate. Accordingly, the fluidic plate may include a plurality of imaging windows 226 configured to align with each of the tissue wells of the well plate 102 to allow each tissue well to be observed from the bottom surface of the fluidic plate 220. In the embodiment shown in FIG. 2, the windows 226 may be cutouts (e.g., holes) formed in the fluidic plate. In other embodiments, the windows may be formed as a transparent material insert disposed in the fluidic plate. Alternatively, in some embodiments, a fluidic plate may be composed of an optically transparent material capable of allowing imaging of a well without a window.

As shown in FIG. 2, the bottom holding plate 230 is configured to be positioned on a bottom surface of the fluidic plate 220. The bottom holding plate 230 is configured to fluidly seal each of the fluid channels 224 on their bottom surface, and to provide an inlet for feed media to be introduced into each of the fluid channels. As shown in FIG. 2, the bottom holding plate includes a plurality of media inlet holes 234 that may be configured to allow a media supply tube from a media supply pump or a media manifold (for example, see FIG. 9) to be coupled to the fluid channels 224 on a bottom surface of the bottom holding plate. According to the embodiment of FIG. 2, the media inlet holes 234 are configured to receive gaskets formed on a bottom surface of the fluidic plate 220. That is, as will be discussed further with reference to FIGS. 4 and 5A, each of the fluid channels 224 may include a gasket defining at least one media supply pore projecting from a bottom surface of the fluidic plate. The at least one media supply pore may be aligned with a first end of a fluid channel 224, and at least one waste pore 214 may be aligned with a second, opposite end of the fluid channel. The gaskets may be configured to be received in the media inlet holes such that the bottom holding plate and the fluidic plate may form a fluid tight seal. Media supply lines may be coupled to the media supply pores to supply feed media to each of the tissue wells. In some embodiments, a media manifold may be coupled to each of the media supply pores of the gaskets. For example, each of the gaskets may receive an outlet of a media manifold (for example, see FIG. 9). In some embodiments, the gaskets may deform to fit around a media manifold outlet to create a fluid seal.

According to the embodiment shown in FIG. 2, the well plate 102, pore plate 210, fluidic plate 220, and bottom holding plate 230 cooperate to form a continuous fluid channel from a media supply pore, to a tissue well, and finally to a waste well. The plate stack arrangement allows for simplified mass manufacturing as there are no enclosed internal channels in any of the plates that form a part of the fluid path. Additionally, as the plates may be easily stacked and removed, cleanout of the individual plates may be simplified.

Figure 3:
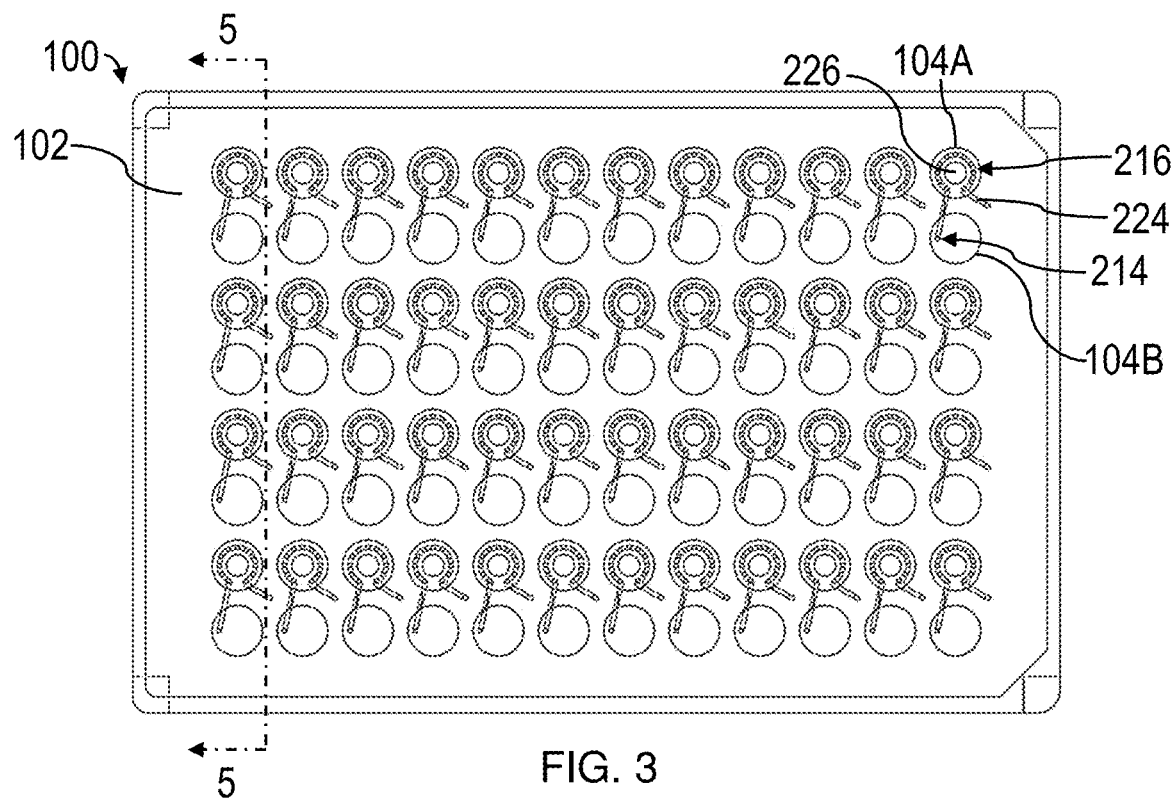
FIG. 3 is a top view of the tissue plate of FIG. 1.
Figure 4:
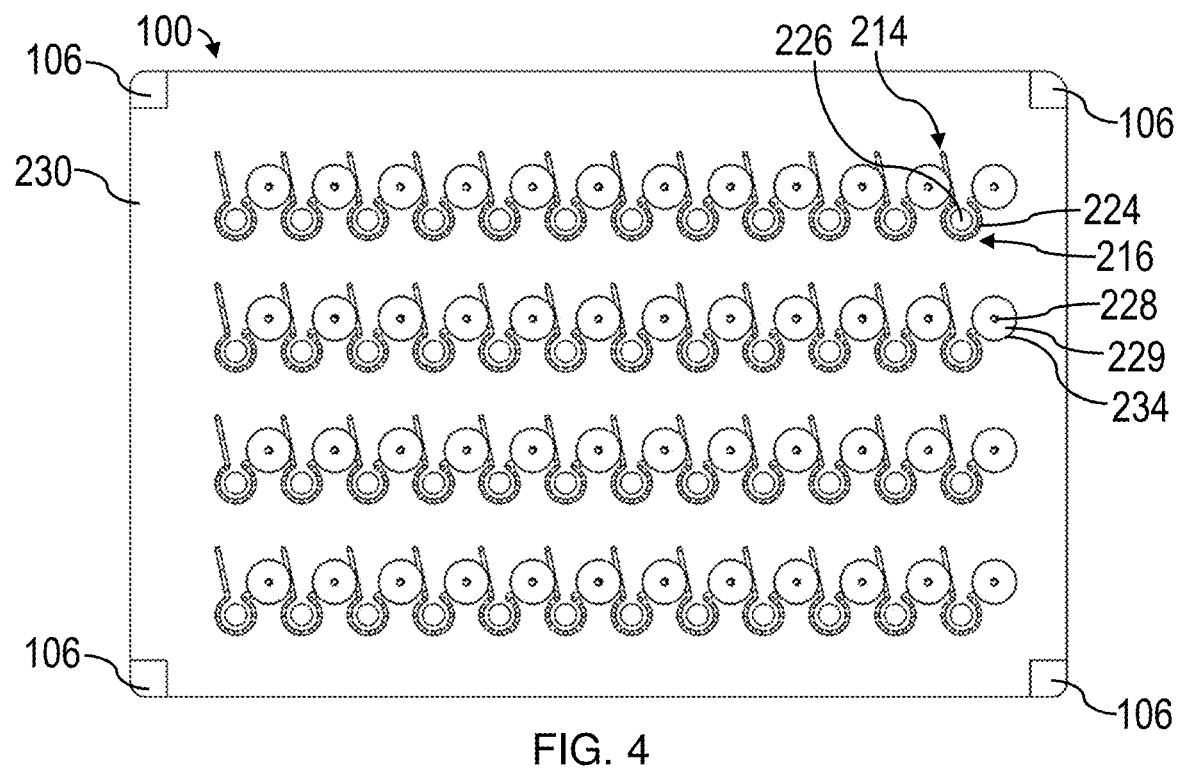
FIG. 4 is a bottom view of the tissue plate of FIG. 1.

FIGS. 3-4 are a top view and bottom view, respectively, of the tissue plate 100 of FIG. 1, better showing the arrangement of the wells, pores, and fluid channels. As discussed previously, each fluid channel 224 extends between and fluidly connects a tissue well 104A to a waste well 104B of a well plate 102 (shown transparently for clarity). According to the embodiment of FIG. 3, the tissue wells 104A and waste wells 104B are disposed in adjacent rows which alternate along the well plate 102. As shown in FIG. 3 and as will be discussed further with reference to FIGS. 5-5A, a plurality of tissue well pores 216 are aligned with a semi-annular portion of the fluid channel 224, and fluidly connect the fluid channel to the tissue well 104A. The tissue well pores 216 overlap with the fluid channel 224 such that fluid may flow from the fluid channel though the tissue well pores. At least one waste well pore 214 (e.g., a single waste well pore) is aligned with an end portion of the fluid channel and fluidly connects the fluid channel to the waste well 104B. An imaging window 226 is positioned such that the fluid channel 224 extends around at least a portion of a perimeter of the imaging window, and allows an optical instrument to view the tissue well 104A from a bottom surface of the tissue plate 100.

As shown in FIG. 4, each fluid channel 224 is aligned with a media supply pore 228 on an end opposite the end aligned with the waste well pore 214. That is, a portion of each fluid channel is aligned with and in fluid communication with the media supply pore 228. Each media supply pore 228 may be defined by a gasket 229 which is disposed in a media inlet hole 234 formed in the bottom holding plate 230. According to the embodiment of FIG. 4, the gasket 229 may be formed of rubber, although any other appropriate material may be employed. In the embodiment shown in FIG. 4, the media supply pores are offset from and do not overlap with either the tissue wells or the waste wells. Accordingly, in the embodiment shown in FIG. 4, a first portion of each fluid channel 224 is aligned with and in fluid communication with an associated media supply pore 228 in the bottom holding plate 230. A second portion of the fluid channel is aligned with and in fluid communication with an associated waste well pore 214 in the pore plate 210. A third, intermediate portion of the fluid channel between the first and second portions is aligned with and in fluid communication with the plurality of tissue well pores 216 formed in the pore plate.

Figure 5:
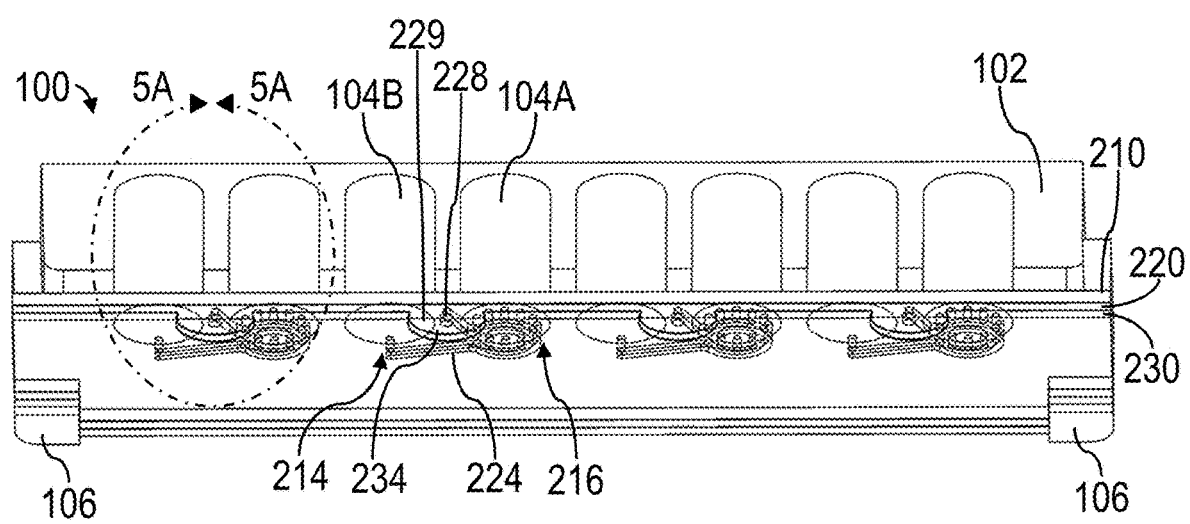
FIG. 5 is a bottom perspective view of a cross-section of the tissue plate of FIG. 3 taken along line 5-5.

FIG. 5 is a bottom perspective view of a cross-section of the tissue plate 100 of FIG. 3 taken along line 5-5, with each of the pore plate 210, fluidic plate 220, and bottom holding plate 230 shown transparently for clarity. As shown in FIG. 5 and discussed previously, the tissue well 104A is disposed adjacent a waste well 104B, which are fluidly connected to one another via a fluid channel 224 formed in the fluidic plate. The pore plate includes at least one waste well pore 214 that fluidly connects the waste well 104B to the fluid channel, while a plurality of tissue well pores 216 are arranged in a semi-circular, or other appropriately shaped, pattern and fluidly connect the fluid channel to the tissue well 104A. A media supply pore 228 is disposed in a gasket 229. The gasket is received inside of a media inlet hole 234 formed in the bottom holding plate. Accordingly, a continuous flow path is formed between the media supply pore 228 and the waste well pore 214. Each of the tissue well pores are arranged in parallel with one another, meaning the fluid channel 224 extends continuously from the media supply pore to the waste well pore. Accordingly, each of the tissue well pores provides a bifurcation point for media flow through the fluid channel, allowing media to flow up into the tissue well 104A and continue through the fluid channel 224 simultaneously, as will be discussed further with reference to FIG. 5A. The flow which bifurcates through one or more of the tissue well pores 216 may flow through the tissue well 104A and back into the fluid channel 224 through others of the plurality of the tissue well pores. That is, the flow may bifurcate through some tissue well pores, and the flow that enters the tissue well may subsequently rejoin the flow in the fluid channel 224, creating a concurrent continuous flow of media through both the tissue well 104A and the fluid channel. It should be noted that while the fluid channel 224, pores 214, 216, 228 are shown disposed in a particular arrangement of plates in FIG. 5, other arrangements are contemplated. For example, the pore plate 210 may be omitted, and the waste well pores 214 and tissue well pores 216 may be disposed in the well plate 102. As another example, the media supply pores 228 may be disposed in the bottom holding plate 230 instead of being formed in a gasket disposed on the fluidic plate 220. As still yet another example, the tissue plate may include a single tissue well pore 216 and/or may include a plurality of waste well pores 214.

Figure 5A:
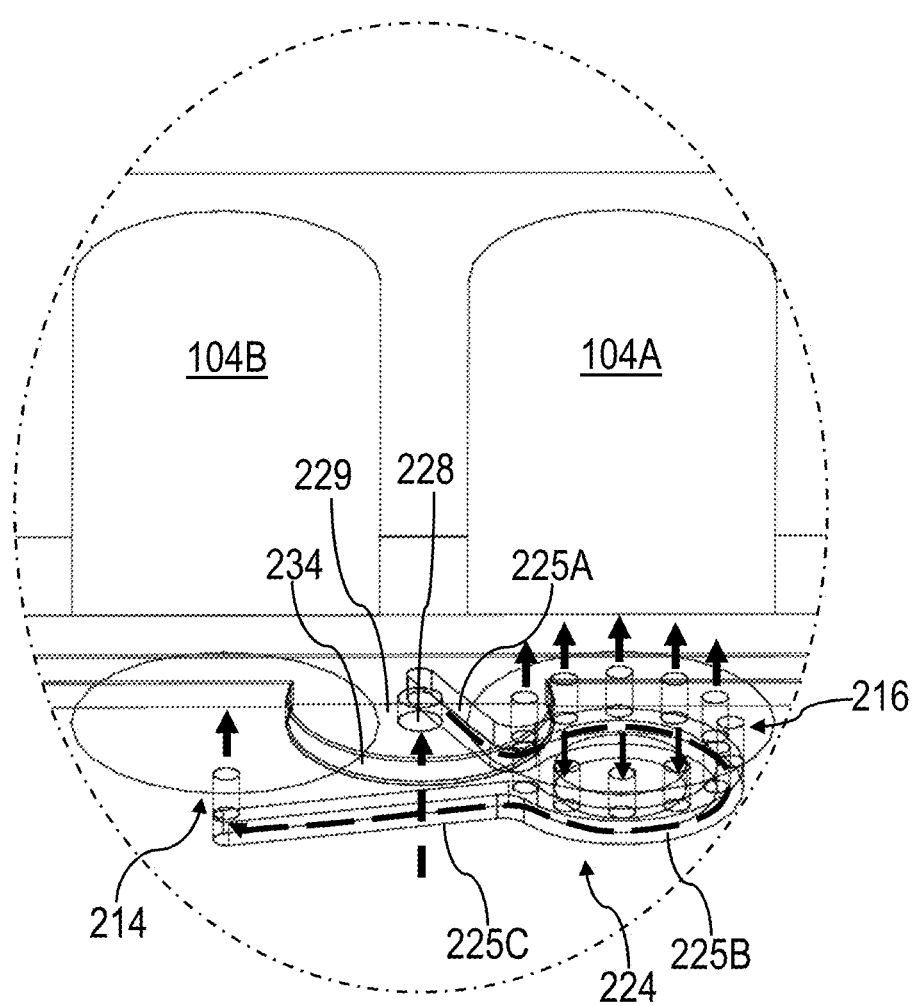
FIG. 5A is an enlarged view of section 5A-5A of the tissue plate of FIG. 5.

FIG. 5A is an enlarged view of section 5A-5A of the tissue plate of FIG. 5 showing the flow path of media through the tissue plate in dashed lines. As shown in FIG. 5A, the media enters a media supply pore 228 which is formed in the gasket 229. The gasket is disposed in a media inlet hole 234 of the bottom holding plate. As shown in FIG. 5A, a first end 225A of the fluid channel 224 is aligned and in fluid communication with the media supply pore 228. As discussed previously, the first end 225A does not overlap with either the tissue well 104A or the waste well 104B. The media flow then flows through the fluid channel 224 to an intermediate portion 225B of the fluid channel. According to the embodiment shown in FIG. 5A, the intermediate portion 225B of the fluid channel is arranged in a semi-annular shape around the bottom of the tissue well 104A. As the media flows through the intermediate portion 225B, some of the media may flow up into the tissue well 104A through the plurality of tissue well pores 216. As each of the tissue well pores 216 are arranged in parallel, media may flow simultaneously through the intermediate portion and each of the tissue well pores. Such an arrangement may promote the vascularization of a tissue layer disposed in the tissue well 104A. Waste media from the tissue layer disposed in the tissue well 104A may also flow from the tissue well 104A through the tissue well pores 216 and into the fluid channel 224, where it may be moved toward a second end 225C of the fluid channel. In some cases, a pressure differential in the intermediate portion of the fluid channel may cause media to flow up (i.e., from the fluidic channel to the tissue well) through the tissue well pores 216 nearest the media supply spore 228, and flow down (i.e., from the tissue well to the fluidic channel) through the tissue well pores nearest the waste well pore 214. The waste well pore 214 is aligned with and fluidly connected to the second end 225C of the fluid channel, such that the waste media may flow from the fluid channel into the waste well 104B. Accordingly, the first end 225A and second end 225C are spaced from one another. The waste media that collects in the waste well 104B may be extracted by a waste extraction pump. In some embodiments, a top cap may be employed which extracts the collected waste media from the waste well 104B. As noted above, each media supply pore 228 may be supplied individually from a media supply pump, such that the flow rate through the fluid channel 224 may be controller and is not affected by media supplied to adjacent tissue wells.

While the fluidic channel of FIG. 5A is shown as a continuous channel from the waste well pore 214 to the media supply pore 228, in some embodiments the fluidic channel may be split into two sections. A first section may extend from a media supply pore to one or more tissue well pores which fluidly connect the first section to a tissue well. A second section may extend from a waste well pore to one or more tissue well pores which fluidly connect the second section to the tissue well. According to this embodiment, media which flows from the media supply pore to the waste well pore is forced to flow through the tissue well, as there is no alternative fluid path which bypasses the tissue well. The tissue well pores connected to the first section are inflow pores for the tissue well, while the tissue well pores connected to the second section are outflow pores for the tissue well.

Figure 6:
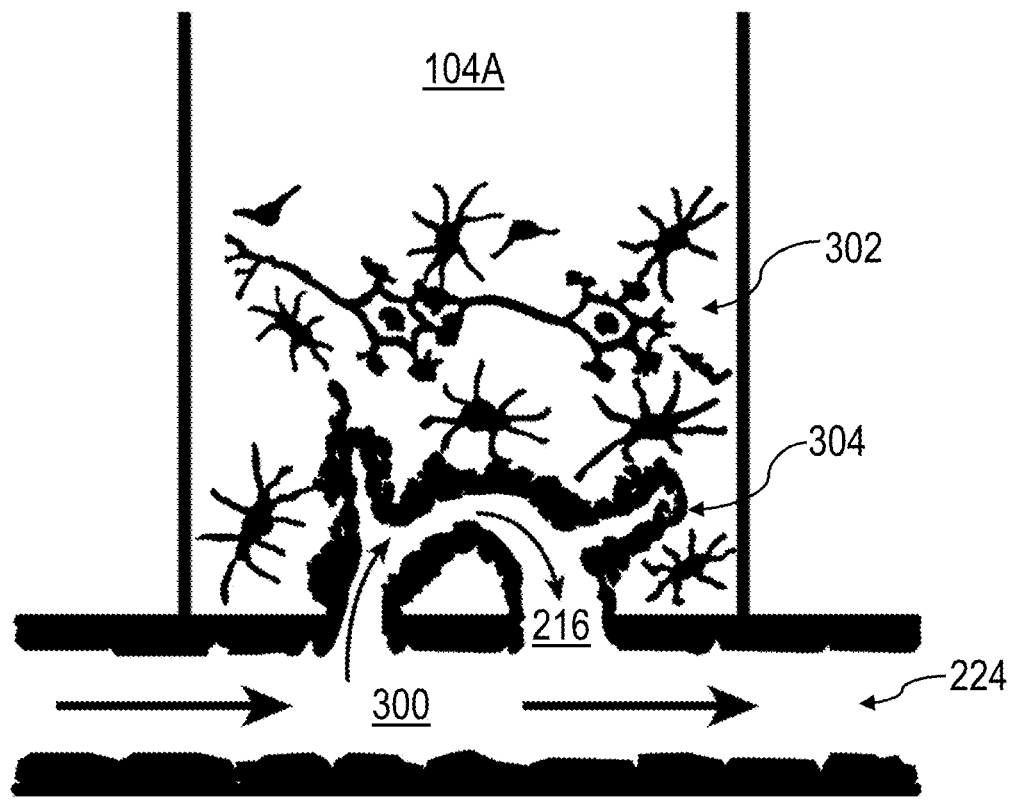
FIG. 6 is a schematic of media flow through an in vitro tissue plate containing vascularized tissue.

FIG. 6 is a schematic of media flow through an in vitro tissue plate containing vascularized tissue 304. As shown in FIG. 6, a tissue layer 302 is disposed in a tissue well 104A. According to the embodiment of FIG. 6, the tissue layer includes a hydrogel and a plurality of living cells. In particular, the living cells may be human neurovascular cells. The tissue layer includes vascularized tissue 304 which may function as an analog to a human blood brain barrier in some embodiments, though other tissues may also be used in some embodiments. As discussed previously, the tissue well 104A is fluidly connected to a fluid channel 224 via a plurality of tissue well pores 216. As the media 300 flows through the fluid channel, some of the media enters the tissue well 104A through a first subset of the tissue well pores 216. The vascularized tissue 304 absorbs nutrients from the feed media and produces waste which is excreted into the flow of media, which flows through a second subset of the tissue well pores back into the fluid channel, and is carried to a nearby waste well for collection and eventual extraction. Such an arrangement may reliably supply the tissue layer with media appropriate to sustain cellular activity in a manner similar to the human body. Accordingly, the arrangement shown in FIG. 6 may be used to test therapeutic compounds and their effect on the living cells such as neurovascular cells. In some embodiments, one or more sensors may be employed to monitor the transendothelial electrical resistance and neuronal activity in the tissue layer 302.

Figure 7:
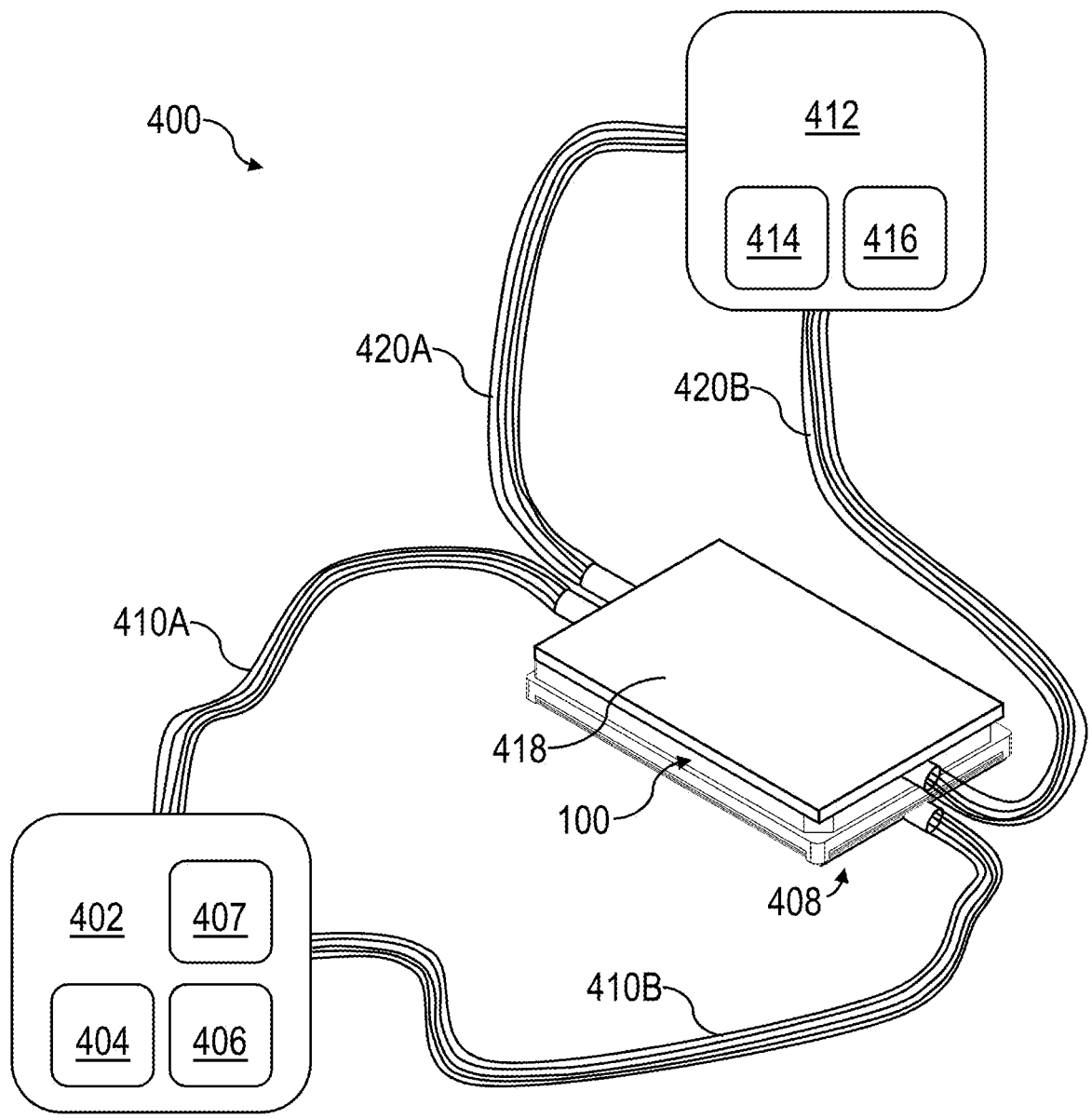
FIG. 7 is a schematic of one embodiment of an in vitro tissue plate, media supply system, and waste extraction system.

FIG. 7 is a schematic of one embodiment of an in vitro tissue plate 100 and media supply and waste extraction system 400. According to the embodiment of FIG. 7, the in vitro tissue plate 100 is similar to that shown in FIGS. 1-5. Media is supplied to the tissue plate, which includes tissue wells, waste wells, and fluid channels configured to support neurovascular cells disposed in each of the tissue wells. As shown in FIG. 7, the media supply and waste extraction system 400 may include two pumps. A media supply pump 402 includes a controller 404 (i.e., a processor executing computer readable instructions disposed on an associated volatile or non-volatile memory) and a media supply reservoir 406. The media supply pump 402 is coupled to a bottom surface of the tissue plate 100 via a plurality of media supply lines 410A, 410B. The media supply lines may be coupled to a media manifold, or otherwise coupled individually to one of a plurality of media supply pores via a media pump bottom cap 408 (e.g., media manifold). Accordingly, the media supply lines may deliver feed media from the media supply reservoir to a tissue well of the tissue plate 100 as the media pump 402 generates flow. In some embodiments, the controller 404 controls a flow splitter 407 that allows flow to be selectively directed to individual media supply lines in a desired sequence. In some embodiments, the controller may direct the flow splitter 407 and media supply pump to sequentially deliver media to individual tissue wells at a predetermined flow rate (e.g., 5 µL/sec). The controller may deliver media to each tissue well in the tissue plate 100 in sequence, so that each tissue well is sufficiently supplied with feed media to sustain cellular activity. For example, feed media may be supplied to a first tissue well for 10 seconds, then a second tissue well for 10 seconds, and so on and so forth until each tissue well is supplied with media. In a tissue plate having 96 total wells (48 tissue wells and 48 waste wells), such a feed cycle may occur over a total duration of approximately 8 minutes. Of course, other appropriate sequences and total feed durations may be employed, as the present disclosure is not so limited. While in the embodiment of FIG. 7, the flow splitter 407 is disposed in the media pump 402, in other embodiments the bottom cap 408 may include the flow splitter, such that media may be provided via a common supply line to the bottom cap 408. Alternatively, a separate flow splitter located between the media pump and the in vitro tissue plate is also possible.

As shown in FIG. 7, the media supply and waste extraction system may also include a waste extraction pump 412 having a waste pump controller 414 (i.e., a processor executing computer readable instructions disposed on volatile or non-volatile memory) and a waste collection reservoir 416. Similar to the media supply pump, a plurality of waste extraction lines 420A, 420B are each connected to individual waste wells and/or separate structures used for collecting the waste using the waste extraction top cap 418. In either case, waste media disposed in each waste well of the tissue plate 100 may be extracted from the waste well and pumped to the waste collection reservoir. For example, in some embodiments, the top cap 418 may include a plurality of tubes which extend from the top cap into each of the waste wells of the tissue plate 100. In one embodiment, the top cap 418 may include a single tube for each waste well. In other embodiments, the top cap may include multiple tubes for each waste well. In some embodiments, the waste pump controller 414 may control the waste extraction pump 412 to extract waste media from each waste well in sequence in cooperation with the media supply pump 402. In other embodiments, the waste media may be extracted from each waste well simultaneously. In such an arrangement, the waste extraction pump may be configured to maintain a pre-determined level of waste media in each waste well.

Figure 8:
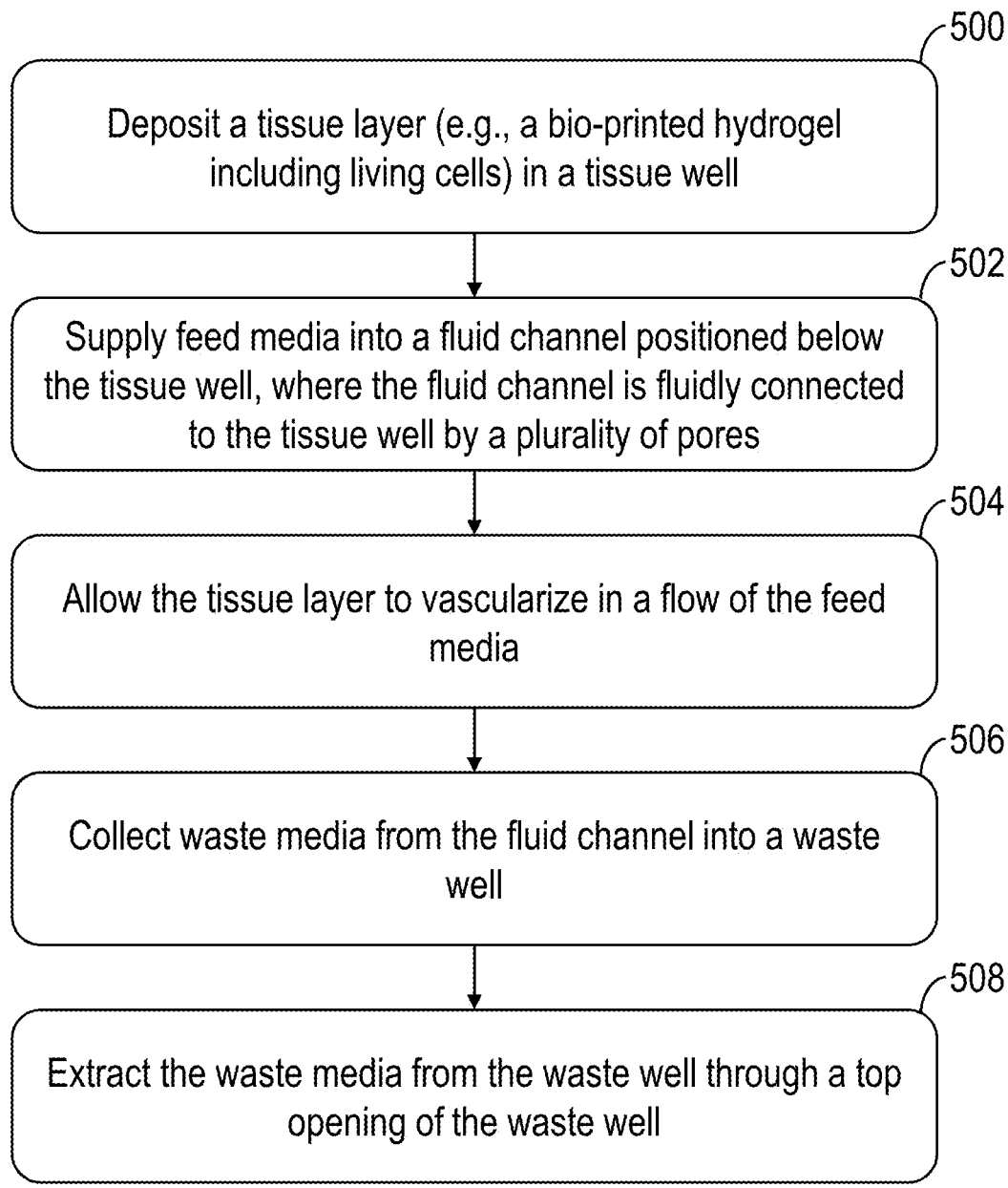
FIG. 8 is a flow chart for one embodiment of a method of using an in vitro tissue plate as described herein.

FIG. 8 is a flow chart for one embodiment of a method of using an in vitro tissue plate of exemplary embodiments described herein. Starting at block 500, a layer of tissue may be deposited in a tissue well of a well plate. The tissue layer may be bioprinted, and may include both a hydrogel and a plurality of living cells (e.g., human neurovascular cells). In some embodiments, multiple tissue layers may be deposited simultaneously in multiple tissue wells. For example, three tissue layers may be deposited simultaneously in three separate tissue wells of the well plate. In some embodiments, depositing the tissue layer may include extruding a hydrogel and living cell mixture into a tissue well. Once the tissue layer is deposited, at block 502 feed media may be supplied into a fluid channel positioned below the tissue well, where the fluid channel is fluidly connected to the tissue well by a plurality of pores. In some embodiments, the feed media may be supplied by a media pump which is coupled to the tissue plate via a bottom cap (e.g., media manifold). The media may be supplied at an appropriate rate to sustain the living cells in the tissue well. In one embodiment, the media may be supplied at a flow rate between 0.5 µL/sec and 5 µL/sec. Supplying the feed media into the fluid channel allows the living cells to vascularize at block 504, and the feed media may bifurcate into a flow through the fluid channel and one or more flows through a first subset of the pores (for example, see FIG. 5A) and that later rejoins the flow within the fluid channel through a second subset of the pores. At block 506, waste media is collected from the fluid channel into a waste well formed in the well plate. Finally, at block 508 the waste media from the waste well is extracted through a top opening of the waste well. In some embodiments, a top cap may be used to extract the waste media with a waste extraction pump.

Figure 9:
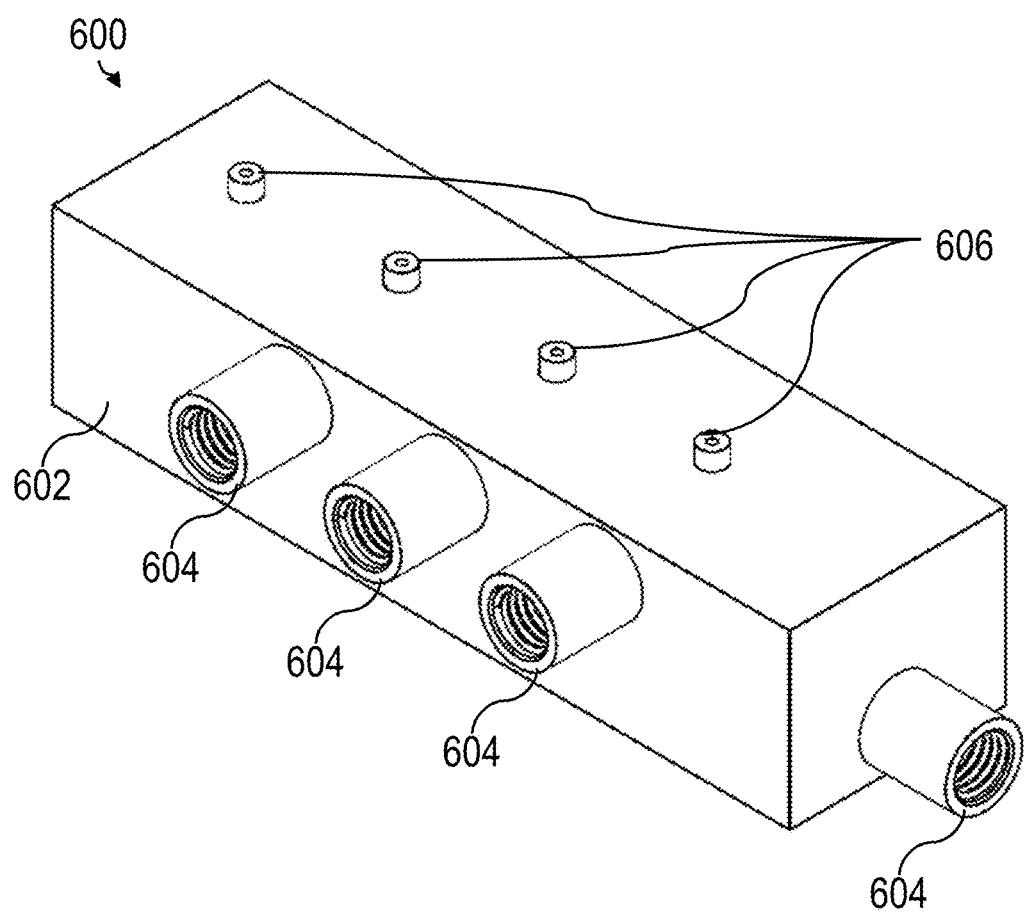
FIG. 9 is a perspective view of one embodiment of a media manifold.

FIG. 9 is a perspective view of one embodiment of a media manifold 600. According to the embodiment of FIG. 9, the media manifold may be configured to connect to a plurality of media supply pores that are formed in gaskets (for example see FIG. 4). As shown in FIG. 9, the media manifold includes a body 602 that contains a plurality of internal fluid channels. The media manifold includes a plurality of ports 604 (e.g., HPLC screw ports), each of which defines a fluid channel to a media manifold outlet 606. Each of the media manifold outlets 606 may be sized and spaced to be received in, or otherwise placed into fluid communication with, corresponding media supply pores disposed on the bottom side of an in vitro tissue plate. That is, each of the media manifold outlets 606 may be inserted into a rubber gasket to create a fluid seal between the media manifold outlet and a media supply pore. According to the embodiment of FIG. 9, each of the ports may be in fluid communication with a single media manifold outlet, so that flow of media to each tissue well in an associated in vitro tissue plate may be controlled. Separate media supply lines may be connected to each port, so that multiple pumps or a flow splitter may control the flow of media that exits each media manifold outlet 606. Of course, while in the embodiment of FIG. 9 the media outlets may be configured to be received by and/or sealed against a rubber gasket, any suitable fluidic connection may be employed, as the present disclosure is not so limited.

While the media manifold of FIG. 9 includes four media outlets, a media manifold may include any suitable number of media outlets to connect to a desirable number of fluid channels in a fluidic plate of an in vitro tissue plate. For example, in some embodiments, the media manifold may include 48 media outlets to connect to each of 48 corresponding fluidic channels in an associated in vitro tissue plate. The media manifold may be 3D printed, molded, assembled, machined, and/or otherwise appropriately constructed with internal channels. The media manifold and internal channels may be coated with parylene or another suitable biocompatible sealant. Such a coating may also ensure the internal 3D printed channels are fluid-tight. Alternatively, the media manifold may be constructed from any appropriate biocompatible material and/or may be coated with an appropriate biocompatible material depending on the particular manufacturing method used to construct the media manifold.

Figure 10:
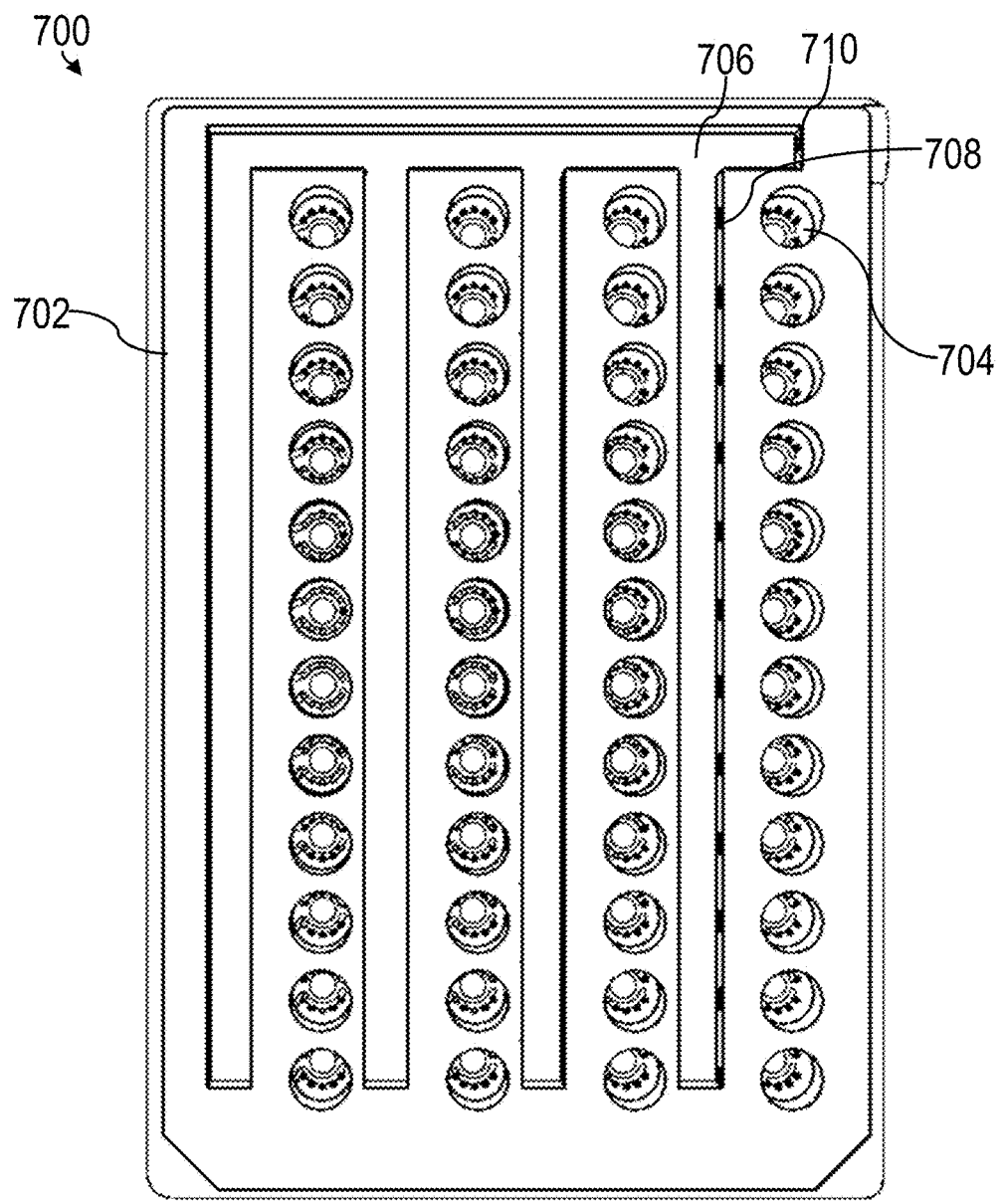
FIG. 10 is a top view of another embodiment of an in vitro tissue plate.

FIG. 10 is a top view of another embodiment of an in vitro tissue plate 700. According to the embodiment of FIG. 10, the in vitro tissue plate includes a plurality of tissue wells 704 formed in a well plate 702. Like the in vitro tissue plate of other exemplary embodiments described herein, the tissue wells are supplied with media via a plurality of tissue well pores. However, in contrast to previously described embodiments, the well plate 702 of FIG. 10 includes a waste channel 706 which allows waste media from the tissue pore to drain continuously without backflow into the tissue well. Rather than individual waste wells for each tissue well, the waste well is shared between all tissue wells. Each tissue well is coupled to the waste channel via a waste pore 708. Waste from the waste channel may be removed via a waste drain 710, allowing the waste media from all of the tissue wells to be removed from the in vitro tissue plate simultaneously via single line. Of course, any suitable number of lines or drains may be used to remove waste from the waste channel, as the present disclosure is not so limited.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An in vitro tissue plate, comprising:
   a well plate including at least two wells, wherein the at least two wells include a tissue well and a waste well; and
   a fluidic plate disposed on a bottom surface of the well plate, wherein the fluidic plate includes a fluid channel extending between and fluidly connected to the tissue well and the waste well, wherein the fluid channel is connected to the tissue well via a plurality of tissue well pores, and wherein the plurality of tissue well pores are disposed at different locations along a length of the fluid channel.

2. The in vitro tissue plate of claim 1, wherein the fluid channel is connected to the waste well via one or more waste well pores.

3. The in vitro tissue plate of claim 2, wherein the plurality of tissue well pores and the one or more waste well pores are formed in a pore plate disposed between the well plate and the fluidic plate.

4. The in vitro tissue plate of claim 2, wherein the plurality of tissue well pores and the one or more waste well pores are formed in the well plate.

5. The in vitro tissue plate of claim 2, further comprising a media manifold disposed on a bottom surface of the fluidic plate opposite the well plate, wherein the media manifold includes one or more media outlets fluidly connected to one or more media supply pores formed in the fluidic plate and fluidly connected to the fluid channel.

6. The in vitro tissue plate of claim 5, wherein the fluidic plate includes at least one gasket which defines the one or more media supply pores, and wherein the at least one gasket receives the one or more media outlets of the media manifold.

7. The in vitro tissue plate of claim 5, further comprising a media supply pump coupled to the media manifold, wherein the media supply pump is configured to generate a flow from the one or more media outlets to the one or more media supply pores, through the fluid channel, the plurality of tissue well pores, and one or more waste well pores into the waste well.

8. The in vitro tissue plate of claim 1, further comprising a waste extraction pump coupled to the waste well, wherein the waste extraction pump is configured to withdraw fluid from the waste well.

9. An in vitro tissue plate, comprising:
   a well plate including an array of wells, wherein the array of wells includes a plurality of tissue wells and one or more waste wells associated with the plurality of tissue wells; and a fluidic plate disposed on a bottom surface of the well plate, wherein the fluidic plate includes a plurality of fluid channels, wherein each tissue well is fluidly connected to an adjacent waste well by one of the plurality of fluid channels, wherein each tissue well of the plurality of tissue wells is connected to a respective fluid channel of the plurality of fluid channels by a plurality of tissue well pores, and wherein the plurality of tissue well pores are disposed at different locations along a length of the respective fluid channel.

10. The in vitro tissue plate of claim 9, further comprising a media manifold disposed on a bottom surface of the fluidic plate opposite the well plate, wherein the media manifold includes a plurality of media outlets, and wherein each of the fluid channels is connected to at least one of the plurality of media outlets.

11. The in vitro tissue plate of claim 10, wherein each of the fluid channels is connected to at least one of the plurality of media outlets via a media supply pore.

12. The in vitro tissue plate of claim 10, further comprising a media supply pump coupled to each of the media outlets, wherein the media supply pump is configured to generate a flow of media through each media outlet.

13. The in vitro tissue plate of claim 12, wherein the media supply pump is configured to generate flow through each media outlet sequentially.

* * * * *